United States Patent [19]
Kenley et al.

[11] Patent Number: 5,858,239
[45] Date of Patent: Jan. 12, 1999

[54] METHODS AND APPARATUS FOR ADJUSTMENT OF BLOOD DRIP CHAMBER OF DIALYSIS MACHINES USING TOUCHSCREEN INTERFACE

[75] Inventors: Rodney S. Kenley, Libertyville; Douglas L. Wilkerson, Gurnee; Joel DeJesus, Buffalo Grove; Tom L. Brose, Gurnee; Andrew Gebhardt, Lake Zurich; John A. Blasko, Gurnee, all of Ill.

[73] Assignee: Aksys, Ltd., Lincolnshire, Ill.

[21] Appl. No.: 799,227

[22] Filed: Feb. 14, 1997

[51] Int. Cl.[6] .......................... B01D 61/32; B01D 61/30
[52] U.S. Cl. ......................... 210/646; 210/86; 210/143; 210/257.2; 210/744; 210/745; 604/4
[58] Field of Search .................. 210/86, 94, 97, 210/104, 143, 257.1, 257.2, 321.71, 645, 646, 647, 744, 929; 604/4–6, 29; 432/44

[56] References Cited

U.S. PATENT DOCUMENTS

| | | | |
|---|---|---|---|
| 4,756,706 | 7/1988 | Kerns et al. | |
| 4,898,578 | 2/1990 | Rubalcaba | |
| 4,942,514 | 7/1990 | Miyagaki et al. | |
| 5,227,049 | 7/1993 | Chevallet et al. | 210/97 |
| 5,326,476 | 7/1994 | Grogan et al. | 210/929 |
| 5,487,827 | 1/1996 | Peterson et al. | 210/646 |
| 5,503,801 | 4/1996 | Brugger et al. | 422/44 |
| 5,573,502 | 11/1996 | Lecocq et al. | 604/4 |
| 5,591,251 | 1/1997 | Brugger | 95/242 |
| 5,591,344 | 1/1997 | Kenley et al. | 210/646 |
| 5,609,770 | 3/1997 | Zimmerman et al. | 210/143 |
| 5,618,441 | 4/1997 | Rosa et al. | 210/143 |
| 5,620,608 | 4/1997 | Rosa et al. | 604/4 |
| 5,653,887 | 8/1997 | Wahl et al. | 210/745 |
| 5,676,644 | 10/1997 | Toavs et al. | 604/6 |
| 5,679,245 | 10/1997 | Manica | 210/646 |

*Primary Examiner*—Joseph W. Drodge
*Attorney, Agent, or Firm*—McDonnell Boehnen Hulbert & Berghoff

[57] ABSTRACT

A method for raising or lowering the fluid level in a chamber in an extracorporeal circuit of a dialysis machine, such as an air trap or compliance chamber, is provided which uses a touch screen. The user of the machine is prompted to indicate on the touch screen the current or actual level of fluid (e.g., blood) in the drip chamber. The user then touches the touch screen to indicate the level, such as by touching an illustration of the chamber at a level corresponding to the actual level. The control system for the machine determines from the level indicated on the touch screen whether the level in the chamber needs to be raised or lowered, and by how much, and responsively operates chamber level adjustment apparatus (such as pressure adjustment apparatus in air communication with the chamber) to raise or lower the level closer to the proper level.

24 Claims, 11 Drawing Sheets

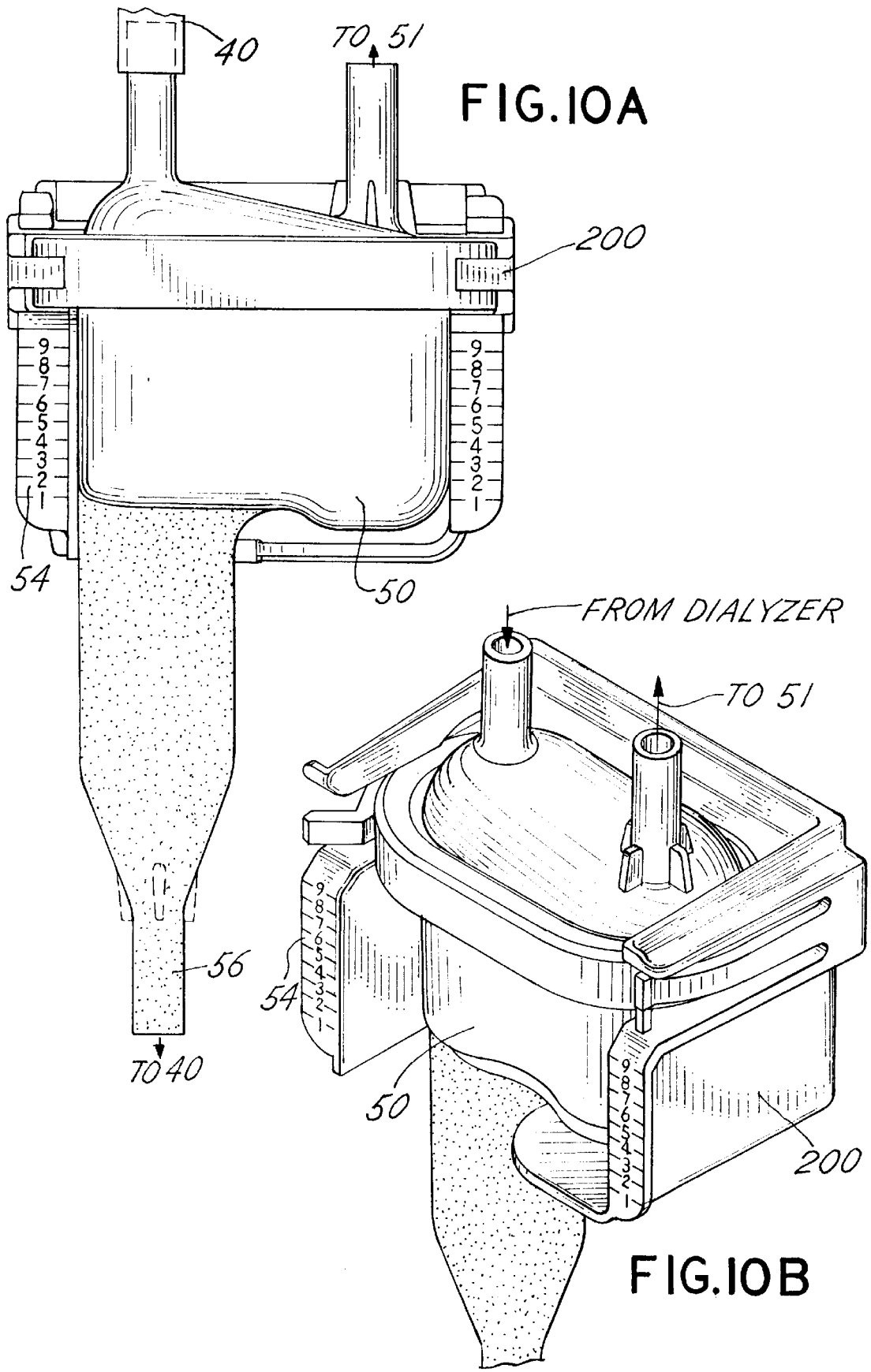

METHODS AND APPARATUS FOR ADJUSTMENT OF BLOOD DRIP CHAMBER OF DIALYSIS MACHINES USING TOUCHSCREEN INTERFACE

BACKGROUND OF THE INVENTION

1. Field of the Invention

This invention relates to dialysis machines, and more particularly to hemodialysis machines that have an extracorporeal blood circuit with a chamber that stores a quantity of blood.

2. Description of Related Art

Dialysis machines are used for treating patients with inadequate kidney function. Hemodialysis machines include, among other things, an extracorporeal blood circuit typically comprising an arterial line, a blood pump, a dialyzer and a venous line. Blood is removed from the patient via the arterial line and pumped by the blood pump to the dialyzer, where blood-borne toxins and excess fluids are removed from the patient's blood. The blood is then returned to the patient via the venous line.

Typically, extracorporeal circuits of hemodialysis machines include a blood drip chamber in the venous line which is designed to separate and remove bubbles of air or foam from the blood being returned to the patient. The chamber, sometimes referred to in the art as an "air trap", stores a quantity of blood which is constantly replenished by blood from the dialyzer, as blood is withdrawn from the chamber (typically from the bottom of the chamber) and returned to the patient. It is also common to have blood chambers in the arterial line leading to the dialyzer, especially in single needle dialysis systems.

During the course of the dialysis session, the blood level may rise above or fall below a predetermined or desired level in the chamber (e.g., the middle of the chamber), due to pressure changes in the extracorporeal circuit, changes in the pump rate of the blood pump, accidental occlusion at the blood access site and trapped air in the chamber displacing fluid. Problems can arise if the level goes too high or too low. For example, if the level in the drip chamber becomes too low, excessive foaming may occur or become entrained in the blood. If the level becomes too high, plasma may separate from whole blood and clotting may occur more readily.

In the prior art, adjustment of the level in an air trap was typically accomplished by manually operating valves or pumps that change the level of blood in the chamber, or by manually manipulating up and down buttons on the face of the dialysis machine which control the level adjustment apparatus. For example, the patent to Grogan et al., U.S. Pat. No. 5,326,476, which is incorporated by reference herein, incorporates up and down buttons on the face of the machine that control the operation of arterial and venous valves and a peristaltic pump. The user operates the buttons to raise or lower the level in the chamber.

It has also been proposed to use optical sensors to sense the level of blood chamber and a control system to responsively operate pressure adjustment apparatus to regulate the pressure and hence level in the chamber. See, e.g., the patent to Chevallet et al., U.S. Pat. No. 5,227,048, which is incorporated by reference herein.

The present invention departs from these approaches by using the user interface, and preferably a touch screen, as a way of indicating the current level of blood or other fluid in the air trap and using the central computer system to make adjustments to the level. Touch screen user interfaces are known in the dialysis art, see, for example, the above Grogan et al. patent. The Grogan et al. patent describes using the touch screen to select, enter and confirm certain parametric value changes for the machine. However, the Grogan et al. patent does not recognize the feasibility of using the touch screen to change the level of the drip chamber, and relies on the use of physical buttons on the face of the machine to control the blood chamber level adjustment apparatus.

Usage of the touch screen to adjust the level of a chamber in the extracorporeal circuit has several distinct advantages. First, it consolidates the user's interaction with the machine controls in one location. Second, it avoids the use of the optical sensors (such as described in the above Chevallet et al. patent), and thus is a less costly implementation since no additional hardware is required. Third, the usage of the touch screen and associated hard keys adjacent to the touch screen (described below) allows for backup safety and verification procedures to be implemented in the central computer control system for the machine, particularly where the user interface supplies input signals to a control system comprising host and backup safety central processing units, such as employed in the inventors' preferred embodiment of the invention.

These, and other advantages and features of the invention will become more apparent from the following detailed description of preferred and alternative embodiments of the invention.

SUMMARY OF THE INVENTION

A method for raising or lowering the level of fluid in a chamber storing a fluid such as blood in an extracorporeal circuit in a dialysis machine is provided, which takes advantage of a user interface having, at least in part, a touch screen. The chamber may be a blood drip chamber or air trap, a compliance chamber such as found in a single needle dialysis system, or other type of chamber that stores a quantity of fluid and has an adjustable level.

During the dialysis session, the user may notice (such as by visual observation) that the level in the chamber is significantly above or below a desired or predetermined level in the chamber (such as two thirds full). The touch screen displays a message that prompts the user to press an icon on the screen if they wish to adjust the level of the chamber. The user then presses the icon, and a display appears that allows the user to indicate on the touch screen the current or actual level of fluid (typically blood) in the chamber. The user is prompted to indicate on the touch screen the current level of fluid in the drip chamber. The user then touches the touch screen to indicate the level, such as by manipulating up and down arrows to indicate the level in an illustration of the drip chamber, touching an illustration of the drip chamber at a level corresponding to the actual level, entering a numeric value associated with the current level, or otherwise. The control system for the machine determines from the level indicated whether the fluid level in the chamber needs to be raised or lowered, and by approximately how much, and responsively operates chamber level adjustment apparatus (such as pressure adjustment apparatus) to raise or lower the level to be closer to the desired or predetermined level.

The desired fluid level in the chamber may vary at different times of operation of the machine, depending on the particular mode the machine is in at the time the level is changed. As used herein, the term "predetermined or desired level" means the level that is appropriate for the chamber at the time the level is adjusted. This information is preferably loaded into a memory in the central computer control system for the machine. Additionally, while the fluid in the chamber is ordinarily blood or blood diluted with saline or dialysate solution during dialysis, the method is applicable to other fluids that may be introduced into the chamber, such as saline solution, and where there is a need to adjust the level.

As noted above, the manner in which the current level in the chamber may be indicated on the touch screen can vary in accordance with the invention. In a preferred embodiment, the touch screen invokes on the display an illustration of a chamber and prompts the user to indicate on the chamber a level corresponding to the actual level in the chamber, either by touching the illustration of the chamber or by using up and down arrows. The chamber illustration may be a substantially accurate profile illustration of the blood drip chamber in the dialysis machine. The illustration may further be provided with a set of graduated indicators to assist the user to touch the illustration at the proper level. In addition, the blood drip chamber itself, or else immediately adjacent structure such as the chamber holder, may also be provided with graduated lines or indicators to assist the user to enter the correct information on the touch screen during the level indicating procedure.

In an alternative embodiment, the user is prompted to select on the touch screen a numeric value associated with the current level, such as by scrolling though a range from 0 to 100 with 0 associated with empty and 100 associated with full, or entering a value with a numeric keypad corresponding to a graduated or other indicator on the drip chamber or adjacent structure. In either case, the central computer control system for the machine takes the information as to the current setting indicated by the user, and then determines the duration and speed for level adjustment apparatus to operate to raise or lower the level in the chamber to the desired level. The central computer control system then operates the level adjustment apparatus to bring the level to the desired level.

BRIEF DESCRIPTION OF THE DRAWINGS

In the following detailed description of presently preferred and alternative embodiments of the invention, reference will be made to the accompanying drawing figures, in which like reference numerals refer to like elements in the various views, and in which:

FIGS. 10A and 10B are elevational and perspective views, respectively, of the air trap of FIG. 3 in which graduated indicator are placed on the holder immediately adjacent to the chamber to assist the user in determining the level of fluid in the chamber.

DETAILED DESCRIPTION OF THE PREFERRED EMBODIMENT

Figure 1:
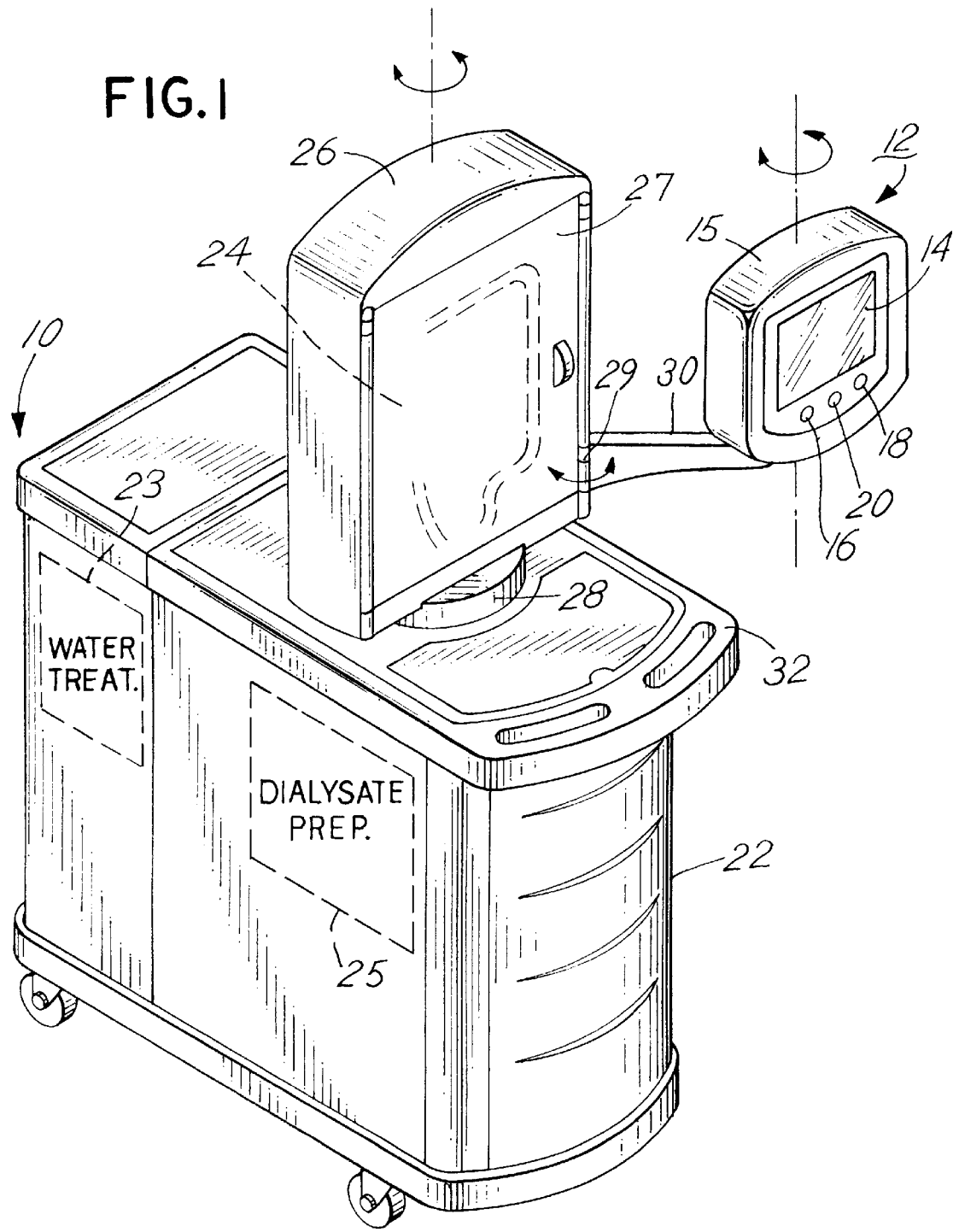
FIG. 1 is an illustration of a dialysis machine, including an extracorporeal circuit and user interface, which may be employed in practicing the invention.

FIG. 1 is an illustration of a dialysis machine 10 having a user interface 12 which may be employed in practicing the invention. The dialysis machine 10 in the preferred embodiment is a machine suitable for use outside of a traditional dialysis clinic setting, such as the home, nursing home or self-care clinic environment. The user interface 12 is designed to be easy to use by a variety of potential users, such as a trained health care professional, a service technician, and especially the patient, a family member of the patient or a helper.

The preferred user interface 12 comprises a touch screen 14, a display positioned immediately behind the touch screen, and a set of three hard keys or buttons 16, 18, 20 positioned below the touch screen 14. The touch screen 14 surface is transparent and physically separate from a display which displays messages, information, pictures, etc. placed behind the surface of the screen. The term "touch screen" is generally used herein to encompass both the touch sensitive surface touched by the user and the display immediately behind the touch screen 14.

The central computer control system 100 for the machine 10 (See FIG. 3) is programmed to display information to the patient or user of the machine concerning the state of machine operation parameters on the display immediately behind the touch screen surface 14. The control system, in cooperation with the hard keys 16, 18, 20 and touch screen, permits the user to change machine settings and enter information and otherwise control the operation of the machine before, during and after the treatment time.

The dialysis machine 10 has a water treatment module 23 and a dialysate preparation module 25 contained within a lower compartment or cabinet 22. These modules 23, 25 play no part in the present invention, and are described in detail in U.S. Pat. No. 5,591,344 to Kenley et al. and assigned to Aksys, Ltd., the assignee of the present invention. The Kenley et al. U.S. Pat. No. 5,591,344 is incorporated by reference herein. Additionally, the manner in which the dialysate solutions are prepared and circulated through the dialysate circuit is not particularly important to this invention and is well known in the art, and may be as described in the Kenley et al. patent, or as described in the above-referenced Grogan et al. patent, or otherwise.

The dialysis machine 10 further includes an extracorporeal circuit 24 mounted above the lower cabinet 22. The extracorporeal circuit is housed behind a door 27 in an enclosure 26 that is mounted to a turntable 28. The turntable 28 is moveably mounted to the top of the lower cabinet 22 such that the turntable 28, enclosure 26 and extracorporeal circuit 24 arc capable of rotation as a unit relative to the lower cabinet 22 about a vertical axis.

The user interface 12 is connected to the machine 10 via a movable arm 30. The proximal end of the moveable arm may be either attached to the enclosure 26 via a hinge 29 as shown, to the rotation assembly 28, or to the lower cabinet 22, such as at a comer of the upper surface of the lower cabinet, e.g., corner 32. Preferably, the user interface arm 30 is connected to the rest of the machine 10 via the hinge 29 or other suitable means such that the arm 30 can rotate about the connection point so as to position the user interface in a convenient orientation relative to a patient sitting or reclining next to the machine, or to a user standing next to the machine such as a nurse or technician. The user interface 12 is incorporated into a rigid housing 15 that mounted to the distal end of arm 30 by a another hinge (not shown) such that the user interface 12 may freely rotate in a vertical plane about a substantially vertical axis on the end of the arm 30. Preferably, the user interface 12 is also mounted to the distal end of the arm 30 via a second hinge or other suitable means for permitting the user interface 12 to rotate about a horizontal axis, i.e., tilt down towards the user (e.g., the patient) if the user is seated or reclining in bed, or up if the user is standing..

Figure 2:
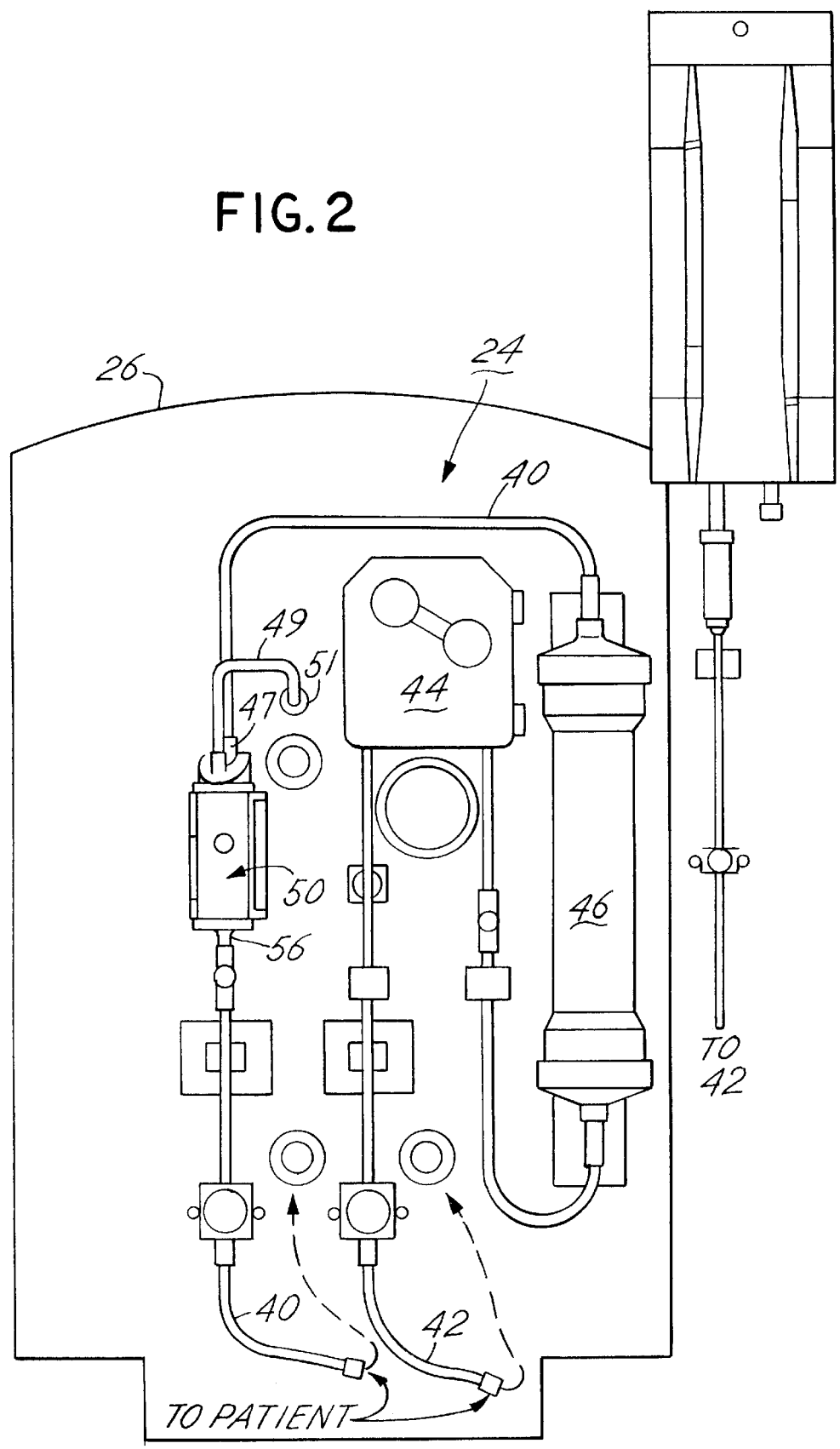
FIG. 2 is a detailed illustration of an extracorporeal circuit of the machine of FIG. 1, showing an air trap or blood drip chamber 50 in the venous line of the extracorporeal circuit.

FIG. 2 is a detailed illustration of the extracorporeal circuit 24 of the machine 10 of FIG. 1, showing an air trap or blood drip chamber 50 in the venous line 40 of the extracorporeal circuit. In the embodiment of FIG. 2, blood is removed from the patient and introduced into the arterial line 42, and pumped by a blood pump 44 to the blood chamber of a dialyzer 46. Blood-borne toxins and excess water are removed from the blood through the membrane of the dialyzer 46 into a dialysate circuit (not shown), and the blood is returned to the patient via the venous line 40. To prevent air from being introduced into the blood being returned to the patient, it is conventional in the dialysis art to place the air trap 50 in the venous line. In the embodiment of FIG. 2, the blood enters the air trap 50 from above via the inlet 47, and is removed from the bottom of the chamber at an outlet 56.

The level of blood in the chamber 50 is subject to fluctuation over the course of a dialysis session, such as due to changes in the blood pressure in the patient, changes in the blood pump rate, air being trapped in the chamber 50, etc. Generally, it is desirable to keep the blood level fairly close to a predetermined and appropriate level (such as approximately the middle of the chamber or slightly above the middle). As noted earlier, the level that is desired may depend on the particular mode that the machine is operating and the particular fluid in the chamber.

To adjust the fluid level, it is known in the art to vary the air pressure in the chamber 50, such as in the manner described in the above cited Chevallet et al. patent, or in the Kenley et al. patent, U.S. Pat. No. 5,591,344. In the embodiment of FIG. 2, a line 49 leads to a port 51. The back side of the port 51 is connected to a line having a pressure sensor, a pump and an air filter, all in series. The pump (not shown) is operated in either the forward or reverse direction to inject air into or out of the chamber 50 via line 49, adjusting the pressure in the chamber and thereby raising or lowering the level of fluid (e.g., blood) in the chamber 50. The rate at which the pump raises or lowers the level in the chamber 50 at different pump speeds will be known when the machine is manufactured, and this information will be stored in memory in the machine computer control system and used as described below.

Further details of the particular extracorporeal circuit illustrated in FIG. 2 are not considered to be pertinent to the operation of the present invention, and can be found in the published PCT application of Kenley et al., publication no. WO 96/25214. A very slightly modified version of the extracorporeal circuit is described in Kenley et al. U.S. Pat. No. 5,591,344.

Figure 3:
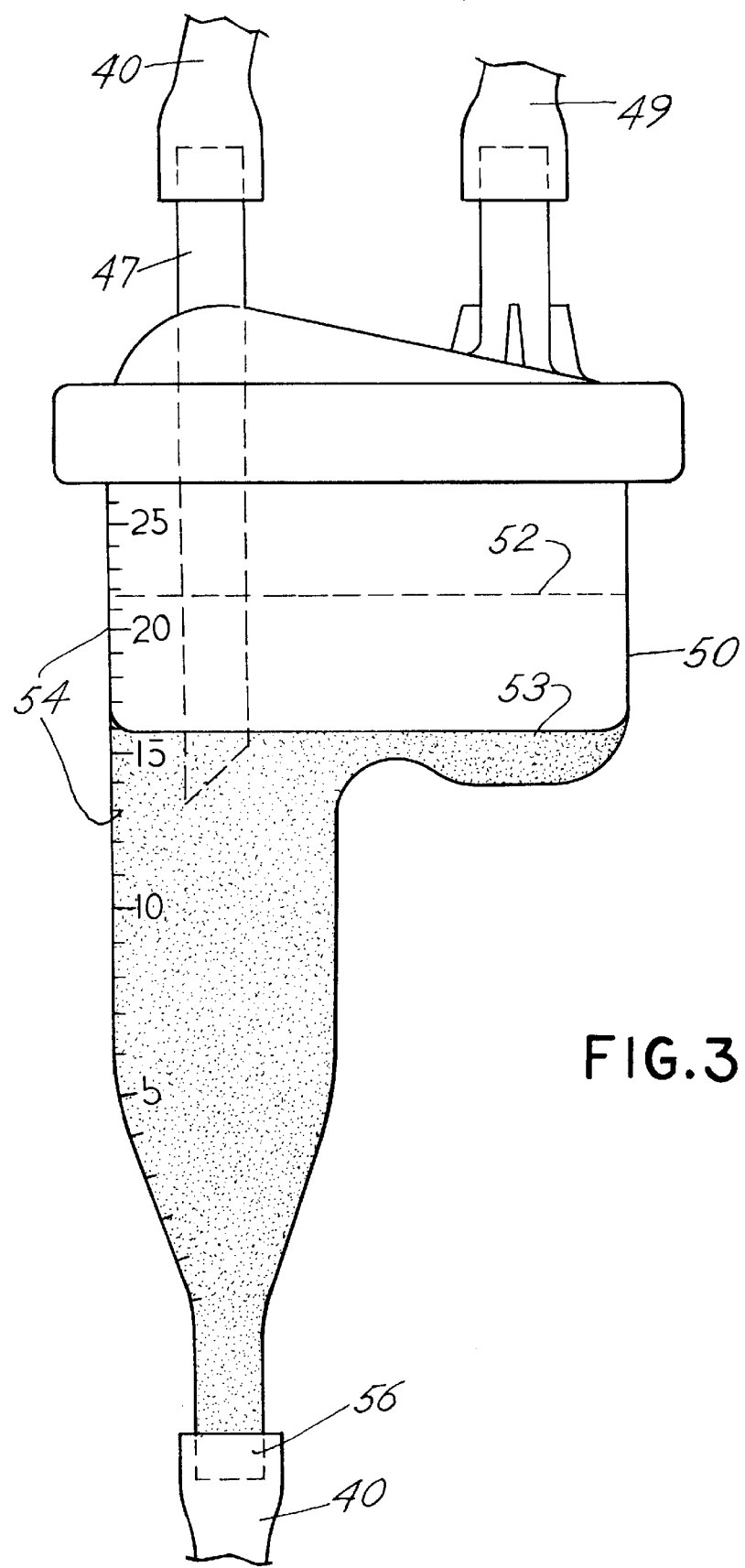
FIG. 3 is an elevational view of a preferred air trap of FIG. 2 for use with the machine of FIG. 1.

FIG. 3 is an elevational view of a preferred air trap 50 for use with the machine of FIG. 1. The chamber 50 is preferably made from a transparent material allowing the user to be able to ascertain the current level of fluid within the chamber. The chamber 50 may have a set of graduated indicators 54 on the exterior surface thereof for assisting said user to accurately gauge the current level of fluid in the chamber. Alternatively, as shown in FIGS. 10A and 10B, the graduated indicators 54 may be applied to flange surfaces of the holder 200 for the chamber 50 or to any other convenient structure positioned immediately adjacent to the chamber 50. The graduated indicators may be simply numbered from 1 (at the bottom) to some arbitrary number (e.g., 25) at the top, and need not necessarily accurately reflect of an actual percentage volume in the vessel. This is assuming that when the user indicates the current level on the touch screen as described below, the level indicated (e.g., "1" in FIG. 10A) is correlated by the computer control system to a meaningful value associated the current level in the chamber 50. For example if the user indicated "1" on the touch screen, the computer control memory may associate an indication of "1" with 35 percent full, or 3 fluid ounces below the desired level, or a pressure adjustment pump operation time of 30 seconds in the forward direction to raise the level to the proper level, or other similar association.

The shape of the drip chamber 50 may dictate how the graduated indicators are arranged relative to the drip chamber 50. While the embodiment of FIG. 3 has indicators 54 extending all the way to the bottom of the chamber 50, it may be necessary to only number the upper portion, as shown in FIGS. 10A and 10B.

In the example of FIG. 3, the current level 53 is considerably below the predetermined or desired level indicated by 52. In this condition, the user will initiate the level adjustment procedure in order to have the fluid level raised closer to the desired level 52.

Figure 4:
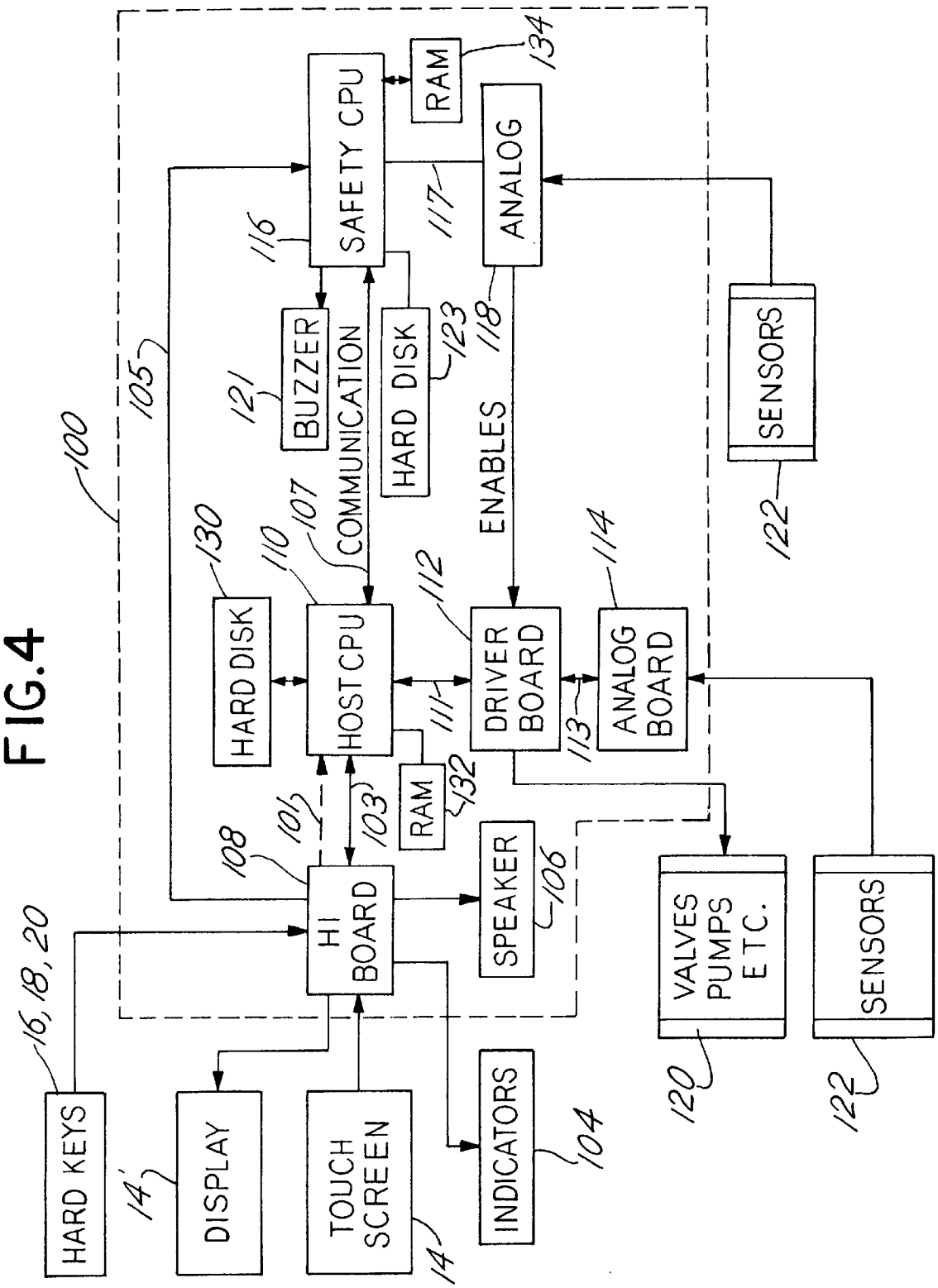
FIG. 4 is a block diagram of a central computer control system governing the operation of the machine of FIG. 1.

FIG. 4 is a block diagram of a computer control system module 100 installed in the machine 10 that governs the operation of the machine and is used in the preferred embodiment to adjust the level in the chamber 50. The module 100 controls the operation of the touch screen 14 to display messages and information concerning the status of the machine to the patient on the display 14', and prompts the user to touch the touch screen 14 in the process of changing parameters or indicating the level of fluid in the drip chamber 50. The touch screen 14 inputs commands or information from the patient into a human interface (HI) board 108, and displaying messages on the display 14' immediately behind the touch screen 14 surface in response to commands from a host Central Processing Unit (CPU) 110 from the HI board 108.

The hard keys 16, 18 and 20 are each a pair of physical, electrically independent and electrically isolated switches. One switch in each of the hard keys 16, 18, and 20 is preferably directly connected, and essentially hard wired, to a backup or safety CPU 116 via a conductor 105, and the other switch in the hard keys is connected to a host CPU 110. The switch for the emergency stop red hard key 20 for the host CPU 110 is preferably directly connected to host CPU 110 from the HI board 108 over a separate conductor, as shown by the dashed line 101.

While FIG. 3 shows the connection between the hard keys 16, 18 and 20 going to the safety CPU 116 via the HI board 108 and conductor 105, the connection between the hard keys and the safety CPU 116 is considered a direct connection since the only function performed by the HI board 108 is debouncing and electrical interfacing the switch signals before they are sent to the Safety CPU 116. The connection is also considered a "direct connection" in the sense the signal path is intentionally designed to not share any circuitry with the Host CPU 110 or the microprocessor on the HI board 108.

The switch for the Red hard key 20 that is directed to the host CPU 110 is directly connected to the host CPU via the HI board 108, which performs debouncing and electrical interfacing, but the signal path does not share any other circuitry on the HI board 108, and the status of the switch is sent to the host CPU over the separate conductor 101 as described above. The switch for the host CPU 110 for the green and blue hard keys 18 and 16, respectively, are subject to debouncing by the microprocessor on the HI board 108, and the status of the switches is sent over the bus 103 connecting the HI board 108 and the host CPU.

A buzzer 121 and set of indicators 104, including lights alert the patient to abnormal conditions in the machine 10, and provide information as to the status of the modes of operation of the machine. The speaker 106 provides for allowing speech output, such as information and instructions to the patient. The indicators 104 receive input signals from the host CPU via the HI board 108. The buzzer 121 receives input signals from the safety CPU 116.

The host CPU 110 is connected via high speed digital data busses 111 and 113 to a driver board 112 and an analog board 114. The host CPU 110 comprises a microprocessor and implements a software program governing the operation of the machine 110 stored in a hard disk 130 or a read only memory (not shown). The hard disk 130 stores other operational information, such as the patient's prescription, data from the sensors in the machine 10, and data input from the patient. An analog board 114 contains analog to digital converters for converting incoming analog signals from the passive sensors in the machine 10 (such as thermistors, pressure sensors and conductivity cells) into digital signals. The driver board 112 receives commands from the host CPU 110 and sends the commands to the valves, pumps, heaters, motors, and other active components of the machines (represented by 120) to cause the components to change their status, e.g., commence or cease operation or change rate, as in the case of a pump, or open and close, as in the case of a valve. The signals from the passive components 122 of the machine, for example, the conductivity sensors, pressure transducers, thermistors, etc. provide their inputs to the analog boards 114 and 118. The CPU 110 and driver board 112 together act as a controller for the active components.

The analog board 118 provides digital information on a bus 117 to the safety CPU 116. The safety CPU 116 acts as watchdog of critical system sensors, and provides enable signals to the driver board 112 that allow certain driver commands to issue to the active components 120 (such as signals to the air pump to raise or lower the level in the drip chamber 50). These features are described in more detail below as they relate to the control of the blood level in the drip chamber 50. Communications between the CPU 116 and host CPU 110 are passed on data bus 107. The safety CPU 116 activates a buzzer or other suitable alarm 121 if certain alarm conditions are present in the machine.

Both the host and safety CPUs 110 and 116 have an associated random access memory 132 and 134, respectively, for use in processing input information from the touch screen 14, for temporary storage of transient data, and for performing other tasks. In a preferred embodiment, the host CPU 110 and hard disk 130 are based on an off-the-shelf IBM compatible personal computer platform with an Intel 386 and 486 microprocessor, or the equivalent.

Figure 5:
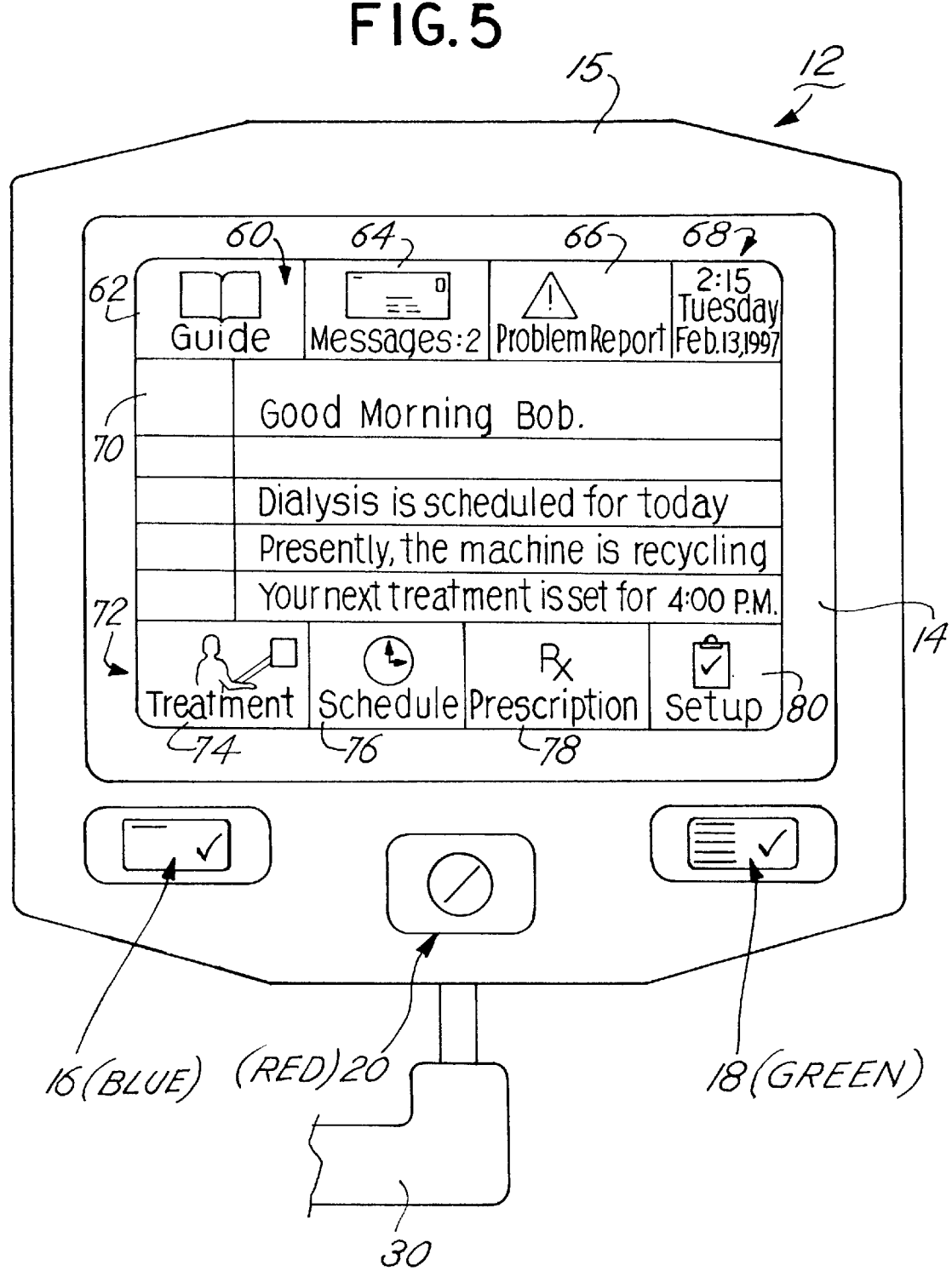
FIG. 5 is an elevational view of the user interface for the machine of FIG. 1.

FIG. 5 is an elevational view of the user interface 12 for the machine of FIG. 1 showing a display on the touch screen 14 prior to the start of the treatment. The particular display shown has an upper portion 60 having an icon 62 for a guide, which allows the user to gain information as to the machine, a messages icon 64 indicating whether the patient has received new messages, a problem report icon 66 providing a means to notify the patient of problems in a non-treatment mode, and a time and day section 68. The middle portion of the display 70 conveys status information to the patient, such as when the next treatment time is to begin. The lower portion 72 has icons that allows the patient to obtain information or enter data as to basic machine and treatment functions, such as a treatment information icon 74, the dialysis schedule icon 76, a prescription icon 78 and a machine set-up icon 80.

When the user wishes to enter information into the machine from any of these menus, the user presses the touch screen 14 to navigate through various screen displays until they arrive at the appropriate screen for the action they wish to take. If the user wishes to input information, such as change the treatment time, they navigate to the appropriate screen (or follow a predetermined pattern of screen displays to get to the desired screen), select the new time with up and down arrows that pop up on the screen (or by other suitable fashion), and then presses the blue hard key 16 off of the touch screen to enter the data. The green hard key 18 is used for confirming entries. The red hard key 20 is an emergency stop key, and when pressed turns all active components into a shut down mode appropriate for the treatment. Further details concerning the operation and function of the user interface 12 are set forth in the patent application of Rodney S. Kenley et al., Ser. No. 08/800,405, filed concurrently, now U.S. Pat. No. 5,788,851 which is incorporated by reference herein.

In accordance with the invention, the touch screen 14 is used in a process to adjust the level of the chamber 50 in the extracorporeal circuit. If the user notices that the level is too low or too high, or is otherwise prompted to change the level in the chamber, the touch screen 14 is used to input information as to the current setting of the chamber 50.

Figure 6:
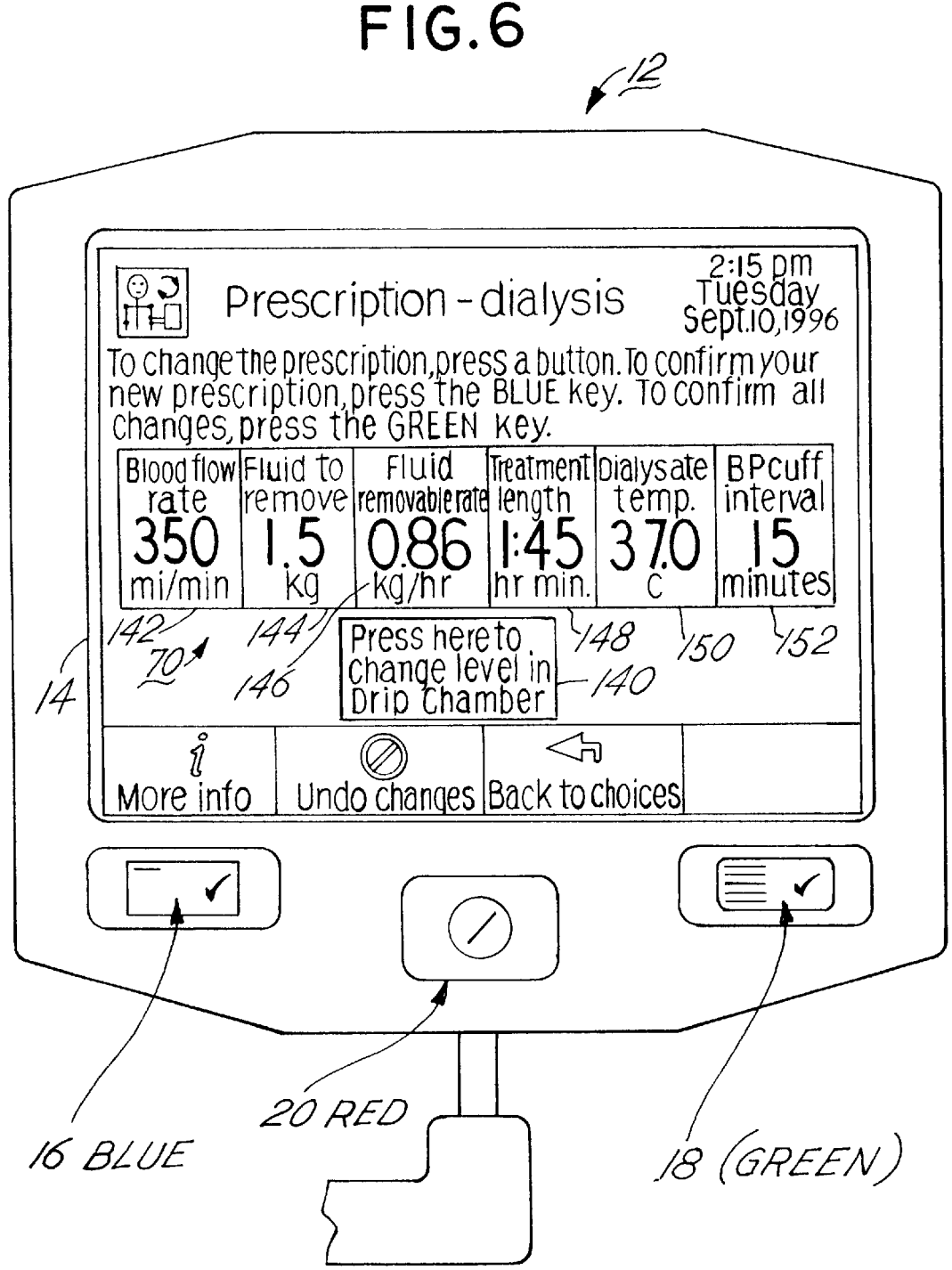
FIG. 6 is an illustration of the user interface of FIG. 5 during the dialysis session, showing the touch screen displaying a message prompting a user to touch an icon on the screen if they wish to change the level of the chamber in the extracorporeal circuit.

FIG. 6 is an illustration of the user interface 12 of FIG. 5 which may be displayed during the dialysis session. The touch screen 14 displays a message prompting a user to touch an icon 140 if they wish to change the level of the chamber 50 in the extracorporeal circuit. The display of FIG. 6 further includes icons 142, 144, 146, 148, 150 and 152 that display current treatment settings in numerical form. The region 154 below the icons 142, 144, etc. can be used to display other information or to allow the patient to navigate to the previous screen, obtain information, or report problems.

The touch screen 14 may display a different message appropriate to a different mode of operation and a prompt to press an icon to change the level in the chamber 50. Thus, the particular screen of FIG. 6 is only one possible example of a screen that displays a message 140 to the user to touch the touch screen if the user wishes to change the level.

Figure 7A:
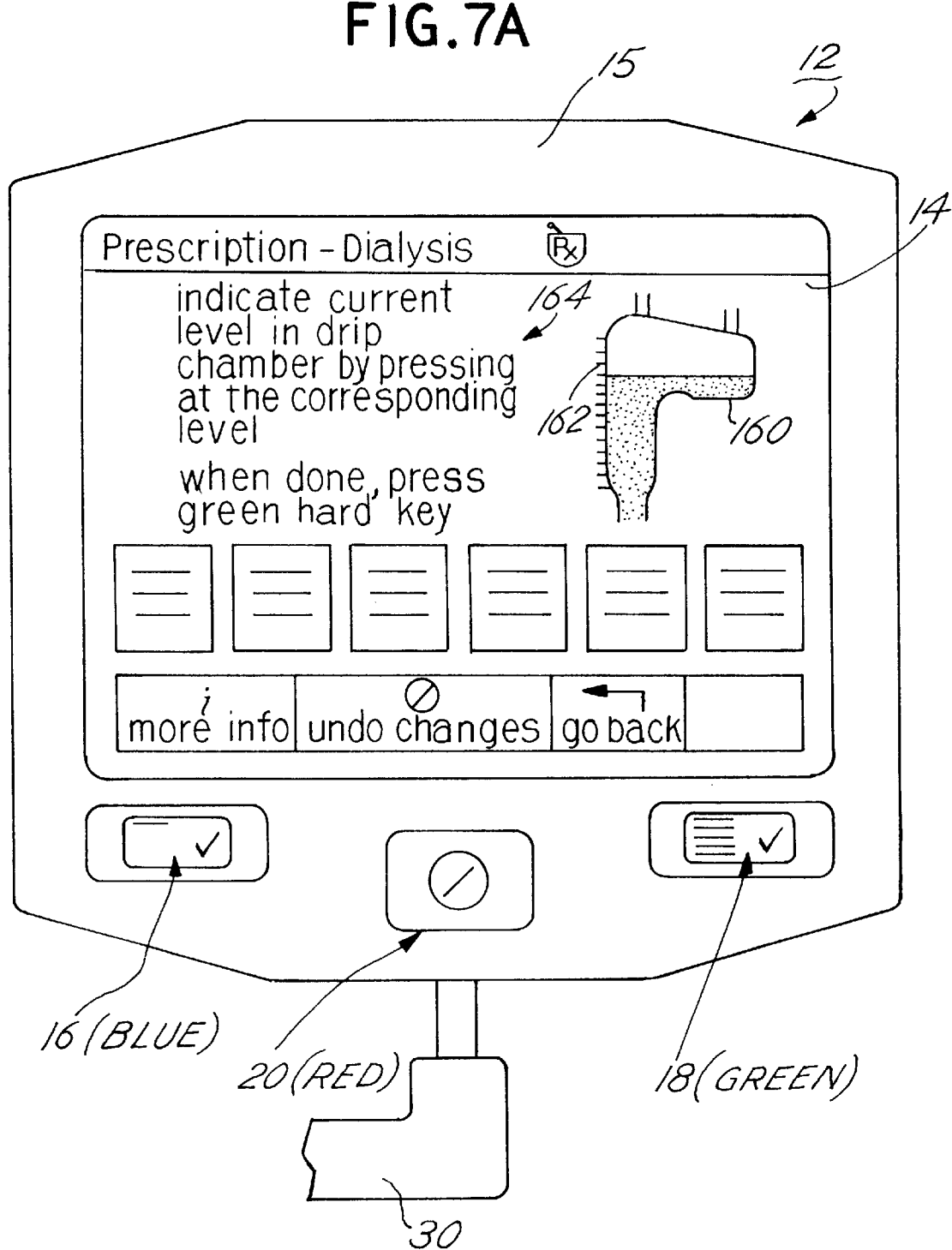
FIG. 7A is an illustration of the user interface of FIG. 5 after the icon 140 of FIG. 6 is touched, showing the touch screen displaying an illustration of the chamber and graduated indicators, assisting the user to touch the illustration at the level that corresponds substantially correctly to the current level.

Once the user presses the icon 140, a display then appears on the touch screen 14 that allows the user to indicate on the touch screen the current level of the chamber 50. Several different possibilities are contemplated for using the touch screen as a means to indicate the current level. One possibility is illustrated in FIG. 7A. When the user presses the icon 140 of FIG. 6, the display of FIG. 7A appears. This display contains an illustration 160 which is a representation of the air trap or chamber 50 in profile along with graduated indicators 162, and a message 164 prompting the user to touch the illustration 160 at a level that corresponds substantially correctly with the current fluid level in the air trap 50. To assist in this process, the graduated indicators 162 may be provided with the illustration 160 to help the user press the level that correctly matches the level in the chamber 50. The usage of graduated indicators 54 on the chamber 50 itself or immediately adjacent structures (see FIG. 3 and FIG. 10A) helps with this process. Upon pressing a spot within the illustration 160, the Host CPU 110 presents a visual indication within the illustration 160 of where the operator pressed (e.g., filling in the illustration 160 from the bottom up to the location where the user pressed). After the user presses the appropriate level on the illustration 160, the user is preferably prompted to press a hard key, e.g., the green confirmation hard key 18.

Figure 7B:
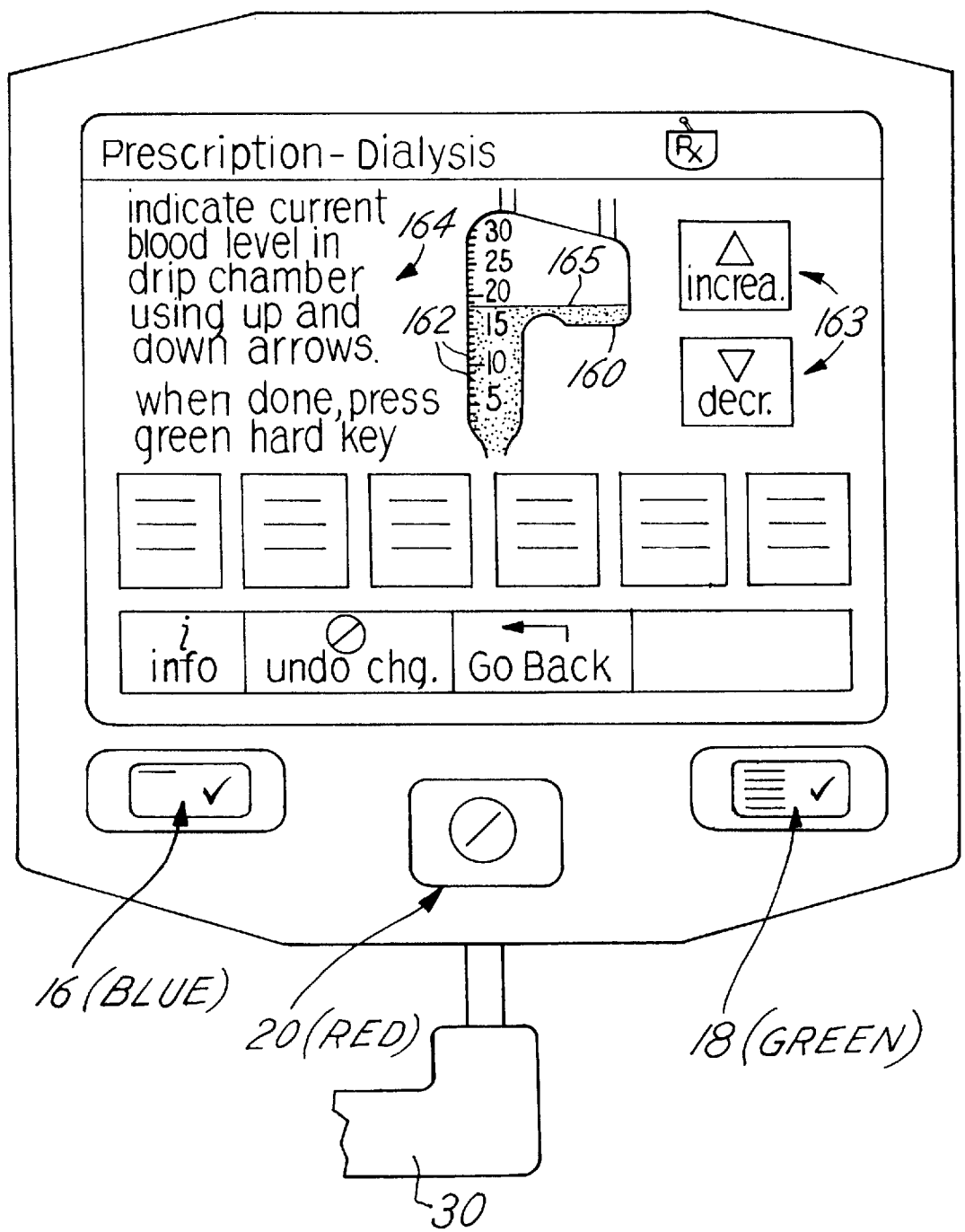
FIG. 7B is an illustration of the user interface after the icon of FIG. 6 is touched, showing an alternative to the procedure of FIG. 7A, in which the touch screen displays an illustration of the air trap in the extracorporeal circuit, graduated indicators, and up and down arrows used to raise or lower the level on the screen to a level corresponding substantially correctly with the current level.

The display of FIG. 7A is particularly appropriate if the size of the touch screen 14 grid is of sufficiently small relative to the size of the illustration 160 that adequate resolution is obtained. If the grid size is too large, then various alternative ways of indicating the level may be used. One preferred way is indicated in FIG. 7B, showing up and down arrows 163 which, when pressed, allow the user to raise or lower the level 165 indicated in the illustration 160 until the level matches the current level in the chamber 50. The illustration 160 need not be exactly identical to the profile of the drip chamber, rather, a representative or approximate likeness in the illustration is sufficient.

Note that in the displays of FIGS. 7A and 7B, some residual information from the previous screen remains, and this is not necessary. For example, when the user presses the icon 140 of FIG. 6, a display completely devoted to a chamber adjustment may appear on the touch screen 14. The display may contain additional information instructing the user as to how to indicate the level, a help or information icon, and a icon allowing the user to go back to the previous display.

The host computer control system 100 (i.e., host CPU 110) determines from the coordinates or location touched on the touch screen (or the level indicated in the illustration using the up and down arrows) the corresponding level indicated in the drip chamber illustration. Such use of position data touched on the touch screen in the embodiment of FIG. 7A is considered conventional and well within the ability of persons of ordinary skill in the art of touch screen displays. The host CPU 110 then compares the level indicated with a predetermined desired level of blood for the chamber 50 for the current mode of operation stored in a memory. For example, the host CPU 110 may determine from the position touched on the touch screen 14 that the blood level in the drip chamber 50 is indicated to be 35% full, and will have stored in memory that the desired level for the chamber in the current mode of operation is 60% full. The host CPU 110 then determines that the level needs to be raised by one fourth of the total volume in the chamber 50. Since the total volume of the chamber 50 will be known in advance and stored in a memory for the computer system (such as on the hard disk 130), and since the rate at which the pressure adjustment pump operates to raise or lower the level in the chamber 50 will also be known in advance and also stored in memory, the host CPU 110 can then determine in straight forward fashion the amount of time the air pressure adjustment pump in line 49 needs to operate to raise the fluid level to the desired level.

The host CPU 110 commands the adjustment pump to operate for the proper amount of time in the proper direction to adjust the current level in the chamber up or down so as to bring the level of blood in the chamber 50 to the predetermined desired level, or at least closer to the desired level if not precisely to the level. Since the pump rate may be variable, the amount of time to run the pump may depend on how fast the pump is run. Further, the desired level may depend on the particular state of the machine, but the host CPU will know what state the machine is in and what the corresponding level should be, since this level for the various states will be stored in memory. The level adjustment is accomplished by the host CPU 110 by calculating from the level indicated on the touch screen 14 both pump time and pump rate parameters, and sending the commands via the driver board 112 to the air pump.

Another possibility of using the user interface to adjust the current level in the air trap 50 will be described in conjunction with FIG. 8, which is an illustration of the user interface after the icon 140 of FIG. 6 has been pressed. This display includes up and down arrows 170 and a numerical display 172. The up and down arrows 170 allow the user to scroll though a range of values corresponding to levels in the air trap. The user scrolls up or down to until the displayed value is correct (for example, "6", with the blood level at opposite the 6 indicator) and corresponds to the actual level in the chamber 50. The user is preferably prompted to confirm the number by pressing the green hard key 18. The information is passed to the computer system (e.g., host CPU 110) for processing, and the calculation of how the level needs to be adjusted proceeds as described above.

Figure 9:
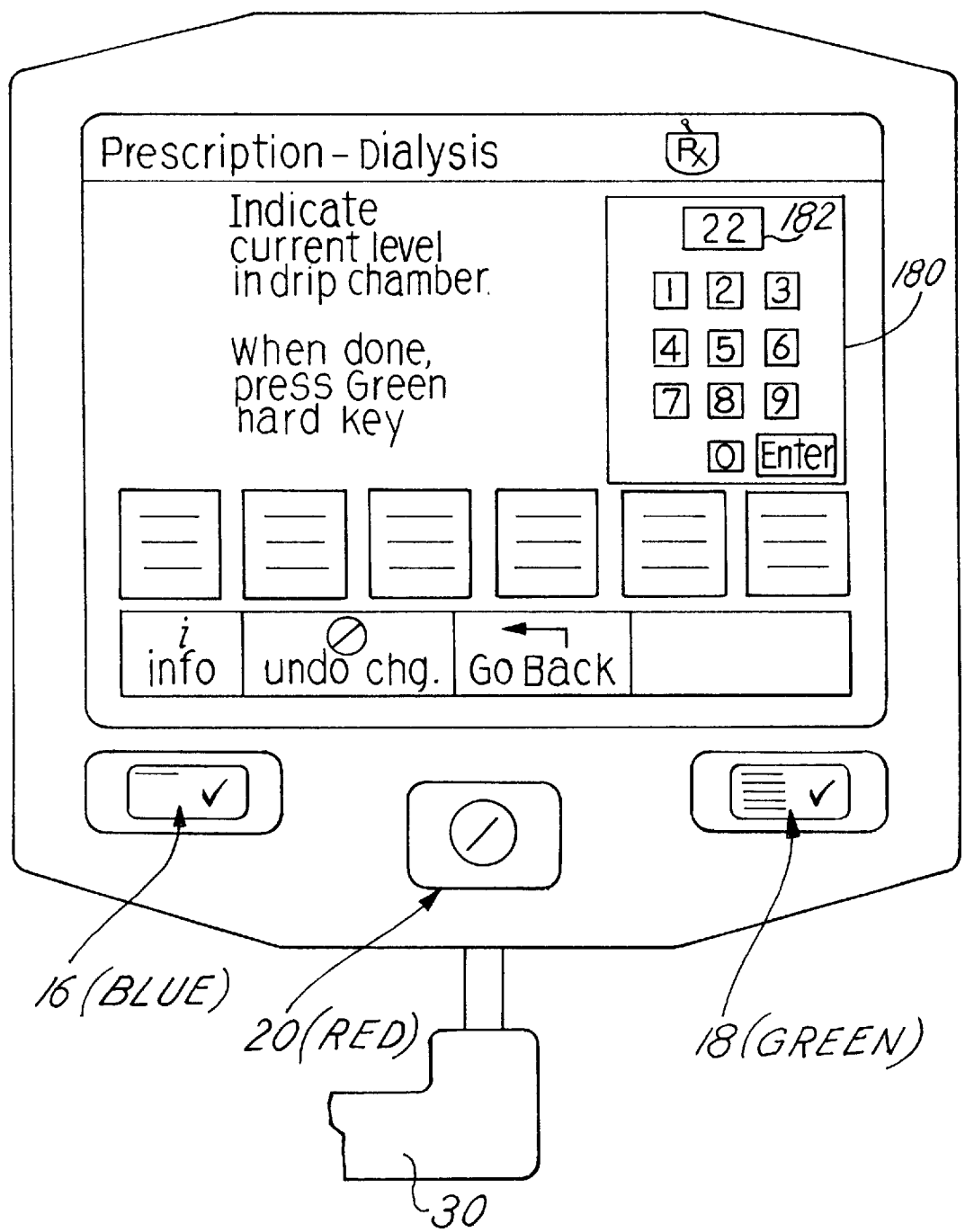
FIG. 9 is an illustration of the user interface of displaying a key pad allowing the user to select and enter a value corresponding to current level in the chamber.

Another possibility is shown in FIG. 9. FIG. 9 is an illustration of the user interface displaying a key pad 180 and a numerical display 182 in response to the pressing of the icon 140 of FIG. 6, allowing the user to select and enter a value on the key pad 180 corresponding to the level in the chamber 50.

Figure 8:
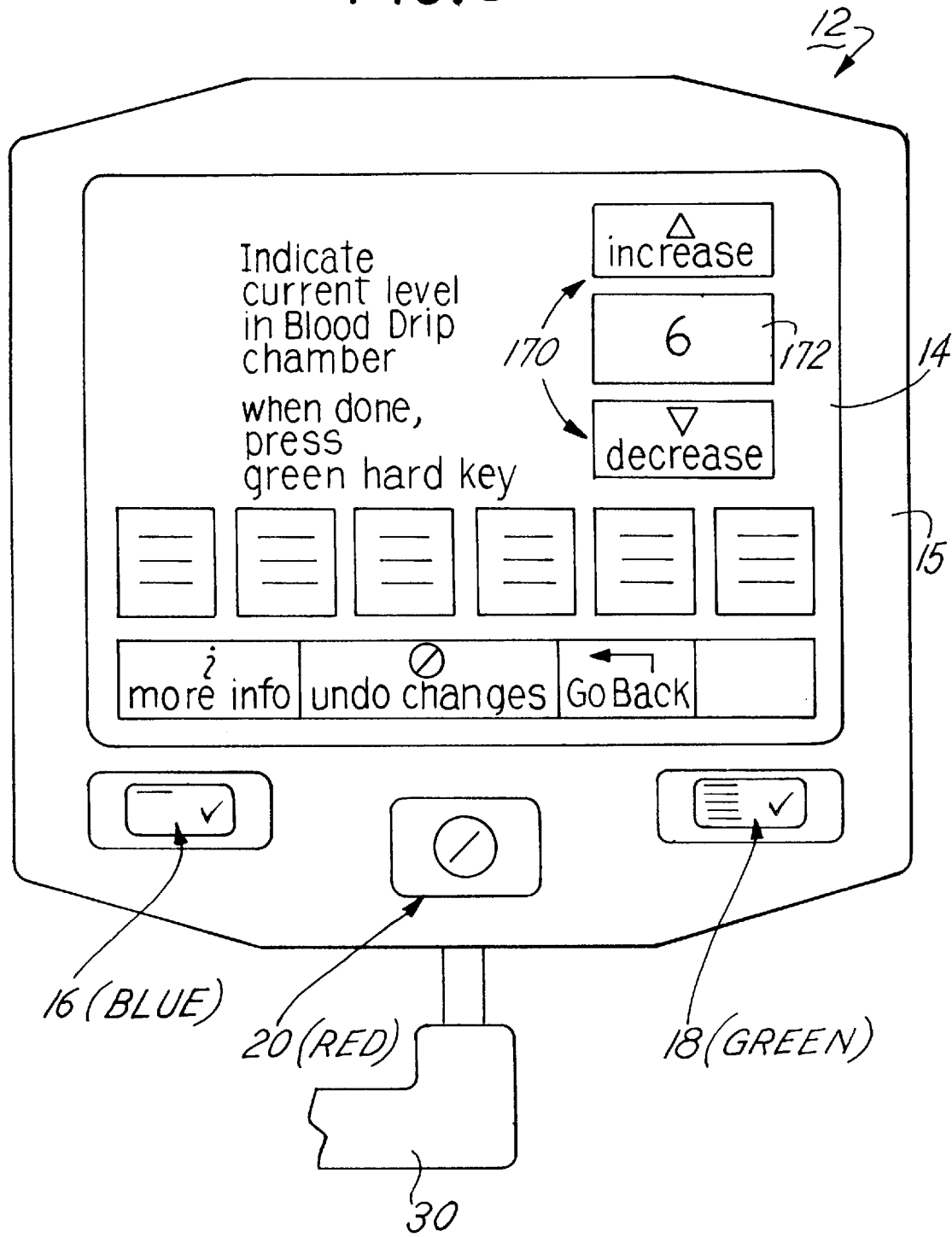
FIG. 8 is an illustration of the user interface displaying up and down arrows allowing the user to scroll though a range of values until a value is displayed that corresponds with the current level in the chamber.

Of the methods shown in FIGS. 7–9, the method of FIG. 7B is preferred in an embodiment where the user interface will primarily be operated by persons other than trained medical professionals, since the display of the blood chamber and the indicating a level corresponding to the actual level is considered intuitively easier than entering numerical values. Instead of displaying an illustration 160 of the chamber as shown in FIGS. 7A and 7B, the host CPU may cause the touch screen 14 to display a generic container that does not physically resemble the air trap, and prompt the user to touch the illustration at the level corresponding to the actual level. Still other types of entry means may still be used.

In a system in which the user interacts solely with the touch screen itself to change parameters, the process of entering the current level could be as straight forward as simply pressing the level on the screen or entering a numerical value and then pressing an ENTER icon on the touch screen. This could be followed up by a pressing of a confirmation icon on the touch screen.

In a more preferred embodiment, the user interacts with the touch screen 14 and one of the hard keys 16, 18, 20 below the touch screen. This embodiment permits extra safety and redundancy features provided by host and safety CPUs to be obtained. A preferred methodology is as follows:

(1) A textual icon 140 on the touch screen 14 will allow the user to access the routine for adjusting the air trap fluid level. See FIG. 6.

(2) Pressing the icon 140 will cause an illustration 160 of the chamber in the extracorporeal circuit to appear on the touch screen. See FIG. 7B. The illustration 160 closely mimics the physical profile of the air trap, thereby allowing the user to relate the actual fluid level in the air trap to a corresponding level in the illustration. Preferably, graduated indicators are present on both the chamber 50 (or adjacent structure) and the illustration 160. See FIGS. 3, 7B, 10A and 10B. The illustration and associated instructions may be superimposed on the previous display, or comprise an entirely new display.

(3) The text 164 on the screen instructs the user to manipulate the up and down arrows 163 to raise or lower the level 165 to the level that corresponds to the actual (current) level in the air trap 50. See FIG. 7B. Note: all of the above activity is provided by the Host CPU 110 software in the machine.

(4) After the proper level is indicated, the Host CPU 110 presents a visual indication within the illustration 160 of where the operator indicated to allow the operator to compare the actual fluid level with the level indicated on the touch screen. The location touched is converted by the host CPU 110 into a current level data word and stored in the host CPU's RAM 132. If the user is unsatisfied, the user presses the up and down arrows 163 to indicate a higher or lower location and the process repeats. The user can manipulate the arrows and illustration 160 as many times as necessary until they are satisfied that the two levels match.

(5) The text 164 on the screen instructs the user to press the Green hard key 18 to begin the physical adjustment of the air trap 50 level when the user is satisfied that the current level has been correctly indicated on screen. Upon pressing the hard key 18, the Host CPU 110 calculates how much air should be added or withdrawn from the air trap in order to bring the level to This is possible since the volume of the air trap 50 is known, and the host CPU 110 knows from the location indicated on the touch screen how much above or below the desired level the current level is.

(6) The Host CPU 110 then requests permission to adjust the level from the Safety CPU 116. An information packet is sent from the Host CPU 110 to the Safety CPU 116 on bus 107 which includes the display screen number, the calculated air pump speed, and the air pump running duration. The information is sent with a cyclical redundancy check (CRC) value that the Safety CPU 116 can use to detect any change in the information.

(7) Upon receipt of the request, the Safety CPU 116 performs its own CRC on the information to check that it matches the Host's CRC value, checks the screen number for consistency with the current operating mode (to be sure the user is allowed to adjust the air trap 50 level), and checks that the identified screen allows air trap adjustment, that the level adjustment pump speed and duration parameters are within acceptable limits, and that the Green hard key 18 has been pressed. If all of the above checks are acceptable, the Safety CPU 116 sends a message to the Host CPU 110 granting adjustment. The Safety CPU 116 will then adjust alarm thresholds on existing protective systems stored in the Safety CPU hard disk 123 to minimize the potential for nuisance alarms while maintaining patient safety.

(8) In response to the grant message from the Safety CPU 116, the Host CPU 110 removes the illustration 160 of the air trap from the display and runs the air trap adjustment pump in line 49 for the calculated time interval in the calculated direction to physically adjust the fluid level in the air trap 50. When the interval expires, the pump stops.

This verification method can be used in any of the level indication screens illustrated in FIGS. 7A–9.

The foregoing method has several features that provide improved safety and performance. First, the Safety CPU 116 allows user requests to adjust the fluid level only at specific times. The Green hard key 18 is employed as a means for preventing a single fault condition in the touch screen (e.g., incorrectly indicating the air trap adjustment level) or a fault in the Host CPU 110 (e.g., requesting invalid adjustment). As noted above, the Green hard key 18 (and the other hard keys 16 and 20) consists of two electrically independent and isolated switches, one routed through microprocessors and software to the Host CPU 110 and the other directly connected and essentially hard wired to the Safety CPU 116. Each processor must detect that the Green hard key 18 has been pressed before the protective system thresholds can be adjusted.

Because raising or lowering the level in the air trap affects protective systems in the blood pathway (e.g., protective systems involving blood pressure, dialyzer inlet pressure and transmembrane pressure), the potential for activating nuisance alarms arises. By using the above approach and hard key interaction, the Safety CPU can know about the intent to adjust the fluid level and take action to avoid nuisance alarms, such a by modifying alarm limits stored in the hard disk 123. Such nuisance alarms implicate serious safety concerns, since nuisance alarms foster indifference to all alarms, serious or not, increasing the potential of the patient to ignore them or become careless in operating the machine. Nuisance alarms also disrupt the treatment and can adversely affect the treatment if the operator shortens the treatment to avoid them.

Persons of skill in the art will appreciate that variations may be made to the preferred and alternative embodiments described above without departure from the true spirit and scope of the invention. For example, the particular design and implementation of the touch screen displays are not critical, nor are the details as the extracorporeal circuit or design of the drip chamber. In an embodiment in which the drip chamber is disposed of after every use, it may be given a simple cylindrical shape and the illustration on the touch screen may be a generic cylinder. Further, the particular level adjustment apparatus used is not critical, and may comprise other equipment besides an air pump in communication with the drip chamber, such as the blood pump, clamps, or other components as appropriate for the particular system in question. The drip chamber need not necessarily be placed in the venous line, as the invention is applicable to chambers generally in extracorporeal circuits, such as in both the arterial and venous lines in single needle dialysis systems. This true spirit and scope is determined by the appended claims, to be interpreted in light of the foregoing.

We claim:

1. A method of adjusting the level of fluid in a chamber in an extracorporeal circuit of a dialysis machine, said chamber in communication with level adjustment apparatus for adjusting the level of fluid in said chamber, said dialysis machine having a user interface comprising a touch screen, comprising the steps of:

(a) prompting a user of said machine to indicate on said touch screen the current level of fluid in said chamber;

(b) in response to said prompting, indicating on said touch screen the current level of fluid in said chamber;

(c) comparing said level indicated at step (b) with a predetermined desired level of fluid in said chamber, and (d) responsively operating said level adjustment apparatus automatically to adjust the current level of fluid in said chamber up or down so as to bring the level of fluid in said chamber closer to said predetermined desired level.

2. The method of claim 1, wherein said step of indicating comprises the step of invoking on said touch screen an illustration of a chamber and indicating a level in said illustration of said chamber corresponding to the current level of fluid in said chamber.

3. The method of claim 2, wherein said illustration comprises an illustration representative of said chamber in said extracorporeal circuit.

4. The method of claim 2, wherein said illustration further comprises an illustration of graduated indicators associated with said illustration.

5. The method of claim 2, wherein said step of indicating a level comprises the step of touching said illustration at a level corresponding to the current level of fluid in said chamber.

6. The method of claim 2, wherein said step of indicating a level comprises the step of providing up and down arrows on said touch screen and raising or lowering said level with said up and down arrows until said level corresponds to the current level of fluid in said chamber.

7. The method of claim 1, wherein said chamber further comprises indicators on the exterior surface thereof for assisting said user to accurately gauge the current level of fluid in said chamber.

8. The method of claim 1, further comprising the step of placing indicators immediately adjacent to said chamber for assisting said user to accurately gauge the current level of fluid in said chamber.

9. The method of claim 1, wherein said step of indicating comprises the step of scrolling with up and down arrows displayed numerical values associated with the current level of fluid in said chamber and stopping said scrolling when a displayed numerical value corresponds to the current level of fluid in said chamber.

10. The method of claim 1, wherein said step of indicating comprises the step of invoking on said touch screen a numeric keypad and touching said numeric keypad so as to select a numerical value corresponding to the current level of fluid in said chamber.

11. The method of claim 1, further comprising the step of confirming the level indicated in step (b), said step of confirming comprising the step of pressing a hard key off of said touch screen user interface, said hard key connected to a back-up central processing unit.

12. A method of adjusting the level of fluid in a chamber of an extracorporeal circuit of a dialysis machine, said dialysis machine having a touch screen user interface, comprising the steps of:

(a) displaying on said touch screen an illustration of said chamber and prompting a user of said machine to indicate on said illustration a location corresponding to the current fluid level in said chamber;

(b) touching the touch screen to indicate in said illustration a level corresponding to the current fluid level in said chamber;

(c) determining, from the location touched in step (b), whether the current level of fluid in said chamber is above or below a predetermined desired level of fluid in said chamber, and responsively (d) raising or lowering said fluid level in said chamber so as to bring said fluid level closer to said predetermined desired level.

13. The method of claim 12, further comprising the step of prompting a user to confirm the level indicated in step (b), and confirming the level indicated in step (b) by pressing a hard key off of said touch screen user interface.

14. The method of claim 13, wherein said dialysis machine comprises a host central processing unit and a backup safety central processing unit, and wherein said hard key off of said touch screen user interface is connected to both said host and safety central processing units.

15. The method of claim 12, wherein graduated indicators are placed on or immediately adjacent to said chamber for assisting a user to accurately gauge the current level of blood in said chamber, and wherein said step of touching the touch screen to indicate in said illustration a level corresponding to the current fluid level in said chamber comprises the step of touching up or down arrows appearing on said touch screen and responsively raising or lowering a fluid level in said illustration.

16. In a dialysis machine, apparatus for adjusting the level of fluid in a chamber in an extracorporeal circuit of said dialysis machine, comprising:

a touch screen;

said touch screen displaying a fluid level setting indication icon and a message prompting a user of said machine to touch said fluid level setting indication icon so as to indicate the current level of fluid in said chamber;

a control system responsive to said touch screen, said control system comparing the current level of fluid indicated on said touch screen with a predetermined desired level of fluid in said chamber and determining whether the fluid level in said chamber should be raised or lowered in order to bring the fluid level closer to said predetermined desired level, and level adjusting apparatus for said chamber responsive to said control system raising or lowering the fluid level in said chamber to bring said fluid level closer to said predetermined desired level.

17. The apparatus of claim 16, further comprising a hard key off of said user interface operatively connected to said control system, said touch screen prompting said user to press said hard key to confirm that the level indicated on said touch screen is the level intended by said user.

18. The apparatus of claim 17, wherein said fluid level setting indication icon comprises an illustration of an air trap in said extracorporeal circuit.

19. The apparatus of claim 16, wherein said fluid level setting indication icon comprises an illustration, and said message prompts said user to indicate on said chamber illustration a level corresponding to said current level of fluid in said chamber in said extracorporeal circuit.

20. The apparatus of claim 16, wherein said fluid level setting indication icon further comprises at least one indicator for assisting said user to touch said chamber illustration at a level corresponding to said current level in said chamber in said extracorporeal circuit.

21. The apparatus of claim 16, further comprising graduated indicators on or immediately adjacent to said chamber in said extracorporeal circuit for assisting said user to accurately gauge the current level of fluid in said chamber.

22. The apparatus of claim 16, wherein said fluid level setting indication icon comprises a set of up and down arrows and a display of a numerical value changeable in response to a pressing of said up and down arrows.

23. The apparatus of claim 16, wherein said fluid level setting indication icon comprises a keypad.

24. A method of adjusting the level of fluid in a chamber of an extracorporeal circuit of a dialysis machine, said dialysis machine having a user interface permitting a user of said dialysis machine to enter commands and information into a central computer system controlling operation of said dialysis machine, comprising the steps of:

(a) prompting a user of said machine to enter via said user interface the current level of fluid in said chamber;

(b) in response to said prompting, operating said user interface to enter information into said central computer system associated with the current level of fluid in said chamber;

(c) comparing with said central computer system said current level indicated at step (b) with a predetermined desired level of fluid for said chamber stored in said central computer system, and (d) commanding with said central computer system a chamber level adjustment apparatus operatively connected to said chamber so as to adjust the current level of fluid in said chamber up or down so as to bring the level of fluid in said chamber closer to said predetermined desired level.

\* \* \* \* \*